United States Patent [19]
Carling et al.

[11] Patent Number: 5,602,125
[45] Date of Patent: Feb. 11, 1997

[54] THIENODIAZEPINE DERIVATIVES AS CHOLECYSTOKININ AND GASTRIN ANTAGONISTS

[75] Inventors: William R. Carling, Bishops Stortford; Victor G. Matassa, Furneux Pelham, both of Great Britain

[73] Assignee: Merck, Sharp & Dohme, Ltd., Hoddesdon, England

[21] Appl. No.: 392,778

[22] PCT Filed: Aug. 20, 1993

[86] PCT No.: PCT/GB93/01782

§ 371 Date: Feb. 28, 1995

§ 102(e) Date: Feb. 28, 1995

[87] PCT Pub. No.: WO94/05673

PCT Pub. Date: Mar. 17, 1994

[30] Foreign Application Priority Data

Aug. 28, 1992 [GB] United Kingdom .................. 9218412

[51] Int. Cl.$^6$ .......................... A61K 31/55; C07D 495/04
[52] U.S. Cl. ............................. 514/221; 540/503
[58] Field of Search ............... 540/503; 514/221

[56] References Cited

U.S. PATENT DOCUMENTS 5,360,802  1/1994  Chambers et al. ............... 540/509

FOREIGN PATENT DOCUMENTS

0514133A1  11/1992  European Pat. Off. .
40-3223290  10/1991  Japan .

OTHER PUBLICATIONS

"Preparation of thienodiazepines as cholecystokinin and gastrin antagonists", Chemical Abstracts, Feb. 17, 1992, vol. 116, No. 7, p. 868, No. 59414e.

"Preparation of thienodiazepines as gastrin antagonists", Chemical Abstracts, Mar. 29, 1993, vol. 118, No. 13, p. 816, No. 124573p.

*Primary Examiner*—Patricia L. Morris
*Attorney, Agent, or Firm*—Robert J. North; Melvin Winokur

[57] ABSTRACT

Thienodiazepine compounds of formula (1) wherein: $R^1$ represents H, optionally substituted $C_{1-6}$ alkyl or $C_{3-7}$ cycloalkyl; $R^2$ represents optionally substituted phenyl; or $R^2$ represents a group (a) where W is $CH_2$ or $NR^9$ and $W^1$ is $CH_2$ or W and $W^1$ are each O; $R^3$ is $C_{3-7}$ cycloalkyl optionally substituted by one or more $C_{1-4}$ alkyl groups, or $R^3$ is $NR^{11}R^{12}$, where $R^{11}$ and $R^{12}$ are each H; $C_{1-12}$ alkyl optionally substituted by $NR^9R^9$ or an azacyclic or azabicyclic group; $C_{4-9}$ cycloalkyl optionally substituted by one or more $C_{1-4}$ alkyl groups; $C_{4-9}$ cycloalkyl$C_{1-4}$ alkyl optionally substituted in the cycloalkyl ring by one or more $C_{1-4}$ alkyl groups; optionally substituted aryl; optionally substituted aryl$C_{1-6}$alkyl; or azacyclic or azabicyclic groups; or $R^{11}$ and $R^{12}$ together form the residue of an optionally substituted azacyclic or azabicyclic ring system; and salts or prodrugs thereof are CCK and/or gastrin receptor antagonists useful in therapy.

9 Claims, No Drawings

THIENODIAZEPINE DERIVATIVES AS CHOLECYSTOKININ AND GASTRIN ANTAGONISTS

This invention relates to thienodiazepine compounds which are useful as antagonists of cholecystokinin and gastrin receptors.

Cholecystokinins (CCK) and gastrin are structurally related peptides which exist in gastrointestinal tissue and in the central nervous system (see, V. Mutt, *Gastrointestinal Hormones*, G. B. J. Green, Ed., Raven Press, N.Y., p.169 and G. Nission, ibid. p.127).

Cholecystokinins include CCK-33, a neuropeptide of thirty-three amino acids in its originally isolated form (see, Mutt and Jorpes, *Biochem. J.* 125, 678 (1971)), its carboxylterminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp-Met-Asp-Phe-NH2, which is the common structural element shared by both CCK and gastrin.

CCKs are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as stimulating colonic motility, gall bladder contraction, pancreatic enzyme secretion and inhibiting gastric emptying. They reportedly co-exist with dopamine in certain mid-brain neurons and thus may also play a role in the functioning of dopaminergic systems in the brain, in addition to serving as neurotransmitters in their own right (see A. J. Prange et al., "Peptides in the Central Nervous System", *Ann. Repts. Med. Chem* 17, 31, 33 [1982] and references cited therein; J. A. Williams, *Biomed Res.* 3 107 [1982]; and J. E. Morley, *Life Sci.* 30, 479 [1982]).

The primary role of gastrin, on the other hand, appears to be stimulation of the secretion of water and electrolytes from the stomach and, as such, is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis.

There are at least two subtypes of cholecystokinin receptors termed CCK-A and CCK-B (T. H. Moran et al., "Two brain cholecystokinin receptors: implications for behavioural actions" *Brain Res*, 362, 175–79 [1986]). Both subtypes are found both in the periphery and in the central nervous system.

CCK and gastrin receptor antagonists have been disclosed for preventing and treating CCK-related and/or gastrin related disorders of the gastrointestinal (GI) and central nervous (CNS) systems of animals, especially mammals, and more especially those of humans. Just as there is some overlap in the biological activities of CCK and gastrin, antagonists also tend to have affinity for both CCK-B receptors and gastrin receptors. Other antagonists have activity at the CCK-A subtype.

Selective CCK antagonists are themselves useful in treating CCK-related disorders of appetite regulatory systems of animals as well as in potentiating and prolonging opiate-mediated analgesia [see P. L. Faris et al., *Science* 226, 1215 (1984)], thus having utility in the treatment of pain. CCK-B and CCK-A antagonists have also been shown to have a direct analgesic effect [M. F. O'Neill et al., *Brain Research*, 534 287 (1990)]. Selective CCK and gastrin antagonists are useful in the modulation of behaviour mediated by dopaminergic and serotonergic neuronal systems and thus have utility in the treatment of schizophrenia and depression (Rasmussen et. al., 1991, *Eur. J. Pharmacol.*, 209, 135–138; Woodruff et. al., 1991, *Neuropeptides*, 19, 45–46; Cervo et. al., 1988, *Eur. J. Pharmacol.*, 158, 53–59), as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value, see e.g. U.S. Pat. No. 4,820,834. Certain CCK antagonists are useful anxiolytic agents and can be used in the treatment of panic and anxiety disorders.

CCK has been reported to evoke the release of stress hormones such as adrenocorticotrophic hormone, β-endorphin, vasopressin and oxytocin, CCK may function as a mediator of responses to stress and as part of the arousal system. CCK-A receptors are now known to be present in a number of areas of the CNS and may be involved in modulating all of the above.

CCK may be involved in the regulation of stress and its relationship with drug abuse e.g. alleviation of the benzodiazepine withdrawal syndrome (Singh et. al., 1992, *Br. J. Pharmacol.*, 105, 8–10) and neuroadaptive processes.

Since CCK and gastrin also have trophic effects on certain tumours [K. Okyama, *Hokkaido J. Med. Sci.*, 206–216 (1985)], antagonists of CCK and gastrin are useful in treating these tumours [see, R. D. Beauchamp et al., *Ann. Surg.*, 202, 203 (1985)].

In the light of discussion in C. Xu et al., *Peptides*, 8, 1987, 769–772, CCK antagonists may also be effective in neuroprotection.

CCK receptor antagonists have been found to inhibit the contractile effects of CCK on iris sphincter and ciliary muscles of monkey and human eyes (Eur. J. Pharmacol., 211(2), 183–187; A. Bill et al., Acta Physiol. Scand., 138, 479–485 [1990]), thus having utility in inducing miosis for therapeutic purposes.

A class of benzodiazepine antagonist compounds has been reported which binds selectively to brain CCK (CCK-B and CCK-A) and gastrin receptors [see M. Bock et al., *J. Med Chem.*, 32, 13–16 (1989)].

European patent application no. 0 167 919 discloses benzodiazepine CCK and gastrin antagonists substituted in the 3-position by, inter alia, a phenyl urea and at the 5-position by, inter alia, a $C_{1-4}$alkyl group.

Japanese patent application no. H3-223290 discloses thienodiazepines having inter alia a phenyl urea substituent and inter alia an aryl or heteroaryl substituent. The compounds are said to be CCK and/or gastrin antagonists.

The present invention provides thienodiazepine compounds of formula (I):

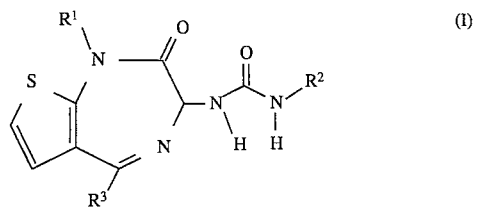

wherein:

$R^1$ represents H, $C_{1-6}$alkyl optionally substituted by one or more halo, $C_{3-7}$cycloalkyl, cyclopropylmethyl, $CH_2CO_2R^5$ (where $R^5$ is $C_{1-4}$alkyl) or $CH_2CONR^6R^7$ (where $R^6$ and $R^7$ each independently represents H or $C_{1-4}$alkyl, or $R^6$ and $R^7$ together form a chain $(CH_2)_p$ where p is 4 or 5);

$R^2$ represents a phenyl group optionally substituted by one or more substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$triazolyl (where q is 0, 1, 2 or 3), 5-hydroxy-4-pyrone, $NR^6R^7$, $NR^9COR^5$, $NR^9COR^9R^5$ (where $R^9$ and $R^{9'}$ are each independently H or $C_{1-4}$alkyl), $CONR^6R^7$ (where $R^6$ and $R^7$ are as previously defined), $SO(C_{1-6}$alkyl), $SO_2(C_{1-6}$alkyl), trifluoromethyl, $CONHSO_2R^8$, $SO_2NHCOR^8$ (where $R^8$ is $C_{1-6}$alkyl, optionally substituted aryl, 2,2-difluorocyclopropane or trifluoromethyl), $SO_2NHR^{10}$ (where $R^{10}$ is a nitrogen containing heterocycle), $B(OH)_2$, $(CH_2)_qCO_2H$, where q is as previously defined; or $R^2$ represents a group

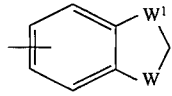

where W represents $CH_2$ or $NR^9$, where $R^9$ is as previously defined and $W^1$ represents $CH_2$, or W and $W^1$ each represent O;

$R^3$ represents $C_{3-7}$cycloalkyl optionally substituted by one or more $C_{1-4}$alkyl groups, or $R^3$ is $NR^{11}R^{12}$, where $R^{11}$ and $R^{12}$ each independently represent H; $C_{1-12}$alkyl optionally substituted by $NR^9R^{9'}$ (where $R^9$ and $R^{9'}$ are as previously defined) or an azacyclic or azabicyclic group; $C_{4-9}$cycloalkyl optionally substituted by one or more $C_{1-4}$alkyl groups; $C_{4-9}$cycloalkyl$C_{1-4}$alkyl optionally substituted in the cycloalkyl ring by one or more $C_{1-4}$alkyl groups; optionally substituted aryl; optionally substituted aryl$C_{1-6}$alkyl; or azacyclic or azabicyclic groups; or $R^{11}$ and $R^{12}$ together form the residue of an optionally substituted azacyclic or azabicyclic ring system; and salts or prodrugs thereof.

It will be appreciated that formula (I) is intended to embrace all possible isomers, including optical isomers, and mixtures thereof, including racemates.

As used herein, the definition of each expression, when it occurs more than once in any structure, is intended to be independent of its definition elsewhere in the same structure.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs" ed. H. Bungaard, Elsevier, 1985.

Halo includes fluoro, chloro, bromo and iodo. Preferably halo will be fluoro or chloro.

As used herein, unless otherwise indicated, alkyl means straight or branched chain saturated hydrocarbon.

As used herein, azacyclic means non-aromatic nitrogen-containing monocyclic, and azabicyclic means non-aromatic nitrogen-containing bicyclic.

Unless otherwise stated, aryl means optionally substituted carbocyclic or heterocyclic aromatic groups, especially phenyl.

Heteroaryl means aromatic rings preferably having 5 or 6 ring atoms and containing at least one atom selected from O, S and N.

A subgroup of compounds according to the invention is represented by compounds of formula (I) wherein $R^1$ represents $C_{1-6}$alkyl, $C_{3-7}$cycloalkyl, cyclopropylmethyl, $CH_2CO_2R^5$ or $CH_2CONR^6R^7$; $R^2$ represents a phenyl group optionally substituted by one or more substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$triazolyl (where q is 0, 1, 2 or 3), 5-hydroxy-4-pyrone, $NR^6R^7$, $NR^9COR^5$, $NR^9COR^9R^5$ (where $R^9$ and $R^{9'}$ are each independently H or $C_{1-4}$alkyl) $CONR^6R^7$ (where $R^6$ and $R^7$ are as previously defined), $SO(C_{1-6}$alkyl), $SO_2(C_{1-6}$alkyl), trifluoromethyl, $CONHSO_2R^8$, $SO_2NHCOR^8$ (where $R^8$ is $C_{1-6}$alkyl, optionally substituted aryl, 2,2-difluorocyclopropane or trifluoromethyl), $SO_2NHR^{10}$ (where $R^{10}$ is a nitrogen containing heterocycle), $B(OH)_2$, $(CH_2)_rCO_2H$, where r is 0, 1 or 2; or $R^2$ represents a group

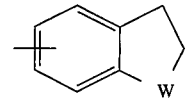

where W represents $CH_2$ or $NR^9$; and $R^3$ represents $C_{3-7}$cycloalkyl or $NR^{11}R^{12}$, where $R^{11}$ and $R^{12}$ each independently represent H, $C_{1-12}$alkyl, $C_{4-9}$cycloalkyl, optionally substituted aryl, optionally substituted aryl$C_{1-6}$alkyl or azacyclic or azabicyclic groups, or $R^{11}$ and $R^{12}$ together form the residue of an azacyclic or a bridged azabicyclic ring system; and pharmaceutically acceptable salts or prodrugs thereof.

When $R^1$ is $C_{3-7}$cycloalkyl, suitable cycloalkyl groups include cyclopropyl, cyclopentyl and cyclohexyl groups, preferably cyclopropyl.

Preferably $R^1$ is $C_{1-6}$alkyl optionally substituted by one or more halo, such as $C_{1-4}$alkyl optionally substituted by 1, 2 or 3 fluoro. Preferred values for $R^1$ include, methyl, n-propyl and isobutyl. More preferably $R^1$ is methyl or n-propyl.

Suitable values for $R^8$ include methyl, ethyl, i-propyl, t-butyl, phenyl and trifluoromethyl.

When $R^8$ is optionally substituted aryl, this will preferably be optionally substituted phenyl. Suitable substituents include $C_{1-4}$alkyl, $C_{1-4}$alkoxy, halo and trifluoromethyl. Preferred is unsubstituted phenyl or phenyl substituted by $C_{1-6}$alkyl, for example, phenyl substituted by $C_{1-6}$alkyl in the ortho position.

When $R^8$ is $C_{1-6}$alkyl, it will preferably represent $C_{1-4}$alkyl. Particularly preferred are methyl and iso-propyl, especially iso-propyl.

When $R^2$ is phenyl substituted by $SO_2NHR^{10}$, suitable values of $R^{10}$ include, for example, thiazole, thiadiazole and pyrazine.

Preferably q is zero.

Preferably $R^2$ is 5-indanyl or phenyl substituted by methyl.

When $R^2$ represents monosubstituted phenyl, the substituent will preferably be located at the 3- or 4-position of the phenyl ring, more preferably the 3position. When $R^2$ represents disubstituted phenyl, the substituents will preferably be located at the 3- and 4-positions. When $R^2$ represents a group

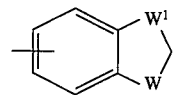

the fused 5-membered ring will preferably be fused across the 3 and 4 positions of the phenyl ring.

When $R^3$ represents $C_{3-7}$cycloalkyl optionally substituted by one or more $C_{1-4}$alkyl, it will preferably represent cyclopentyl, cyclohexyl or cycloheptyl, more preferably cyclohexyl, optionally substituted by one or more methyl.

When $R^3$ represents a group $NR^{11}R^{12}$ where $R^{11}$ or $R^{12}$ represents optionally substituted aryl or optionally substituted aryl$C_{1-6}$alkyl, suitable aryl groups include phenyl, thienyl, furyl, pyrrolyl and pyridinyl, preferably phenyl. Suitable aryl substituents include, for example, $C_{1-4}$alkyl, $C_{1-4}$alkoxy, halo and trifluoromethyl.

When $R^{11}$ or $R^{12}$ represents an azacyclic or azabicyclic group, or $C_{1-6}$alkyl substituted by azacyclic or azabicyclic group, the azacyclic or azabicyclic group may contain, in addition to the nitrogen atom, a further heteroatom selected from O and S, or a group $NR^{13}$ where $R^{13}$ is H or $C_{1-4}$alkyl.

When $R^{11}$ or $R^{12}$ represents an azacyclic group or $C_{1-6}$alkyl substituted by an azacyclic group, the azacyclic group will suitably contain from 5 to 10 ring atoms.

When $R^{11}$ or $R^{12}$ represents an azabicyclic group or $C_{1-6}$alkyl substituted by an azabicyclic group, the azabicyclic group will suitably contain from 7 to 10 ring atoms.

When $R^{11}$ or $R^{12}$ represents $C_{4-9}$cycloalkyl substituted by one or more $C_{1-4}$alkyl groups or $C_{4-9}$cycloalkyl$C_{1-4}$alkyl substituted in the cycloalkyl ring by one or more $C_{1-4}$alkyl groups, the $C_{1-4}$alkyl groups may be located on any available ring carbon atom. In particular, geminal disubstitution is provied for. The $C_{1-4}$alkyl groups will preferably be methyl groups.

Suitably $R^{11}$ and $R^{12}$ are selected from H, $C_{1-6}$alkyl, such as methyl, ethyl and n-propyl, $C_{4-9}$cycloalkyl, such as cyclopentyl, cyclohexyl, cycloheptyl and cyclooctyl, optionally substituted by one or more methyl groups, $C_{4-9}$cycloalkyl$C_{1-4}$alkyl, such as cyclohexylmethyl, aryl$C_{1-6}$alkyl, such as benzyl, $C_{1-6}$alkyl substituted by $NR^9R^{9'}$ such as $CH_2CH_2N(CH_3)_2$, $C_{1-6}$alkyl substituted by an azacyclic group, such as $C_{1-4}$alkyl substituted by morpholinyl, and azacyclic groups, such as N-methylpiperidine.

When $R^{11}$ and $R^{12}$ together form the residue of an azacyclic or azabicyclic ring system, the azacyclic or azabicyclic ring system may contain, in addition to the nitrogen atom to which $R^{11}$ and $R^{12}$ are attached, a second heteroatom selected from O, S or a group $NR^{22}$ where $R^{22}$ is H, $C_{1-4}$alkyl $CO_2R^a$, $COR^a$ or $SO_2R^a$ where $R^a$ is $C_{1-6}$alkyl, optionally substituted phenyl or benzyl optionally substituted in the phenyl ring by one or more substituents, where the phenyl substituents are selected from $C_{1-4}$alkyl, $C_{1-4}$alkoxy, halo and trifluoromethyl.

When $R^{11}$ and $R^{12}$ together form the residue of an azacyclic ring system, the ring system may be substituted by one or more groups selected from $C_{1-6}$alkyl, $C_{1-6}$alkoxy, hydroxy, halo, trifluoromethyl, oxo, $SR^5$, $NR^6R^7$, $NR^9C_{1-4}$alkyl$R^{23}$, $=NOR^9$ or

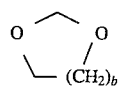

where $R^6$, $R^7$, $R^9$ and $R^5$ are as previously defined, $R^{23}$ is halo or trifluoromethyl, and b is 2 or 3. The substituents may be located on any available carbon atom. In particular, geminal disubstitution is provided for where appropriate. Particularly suitable substituents include oxo, ketyl, $C_{1-6}$alkyl, $C_{1-6}$alkoxy, trifluoromethyl and $NHC_{1-4}$alkyl$CF_3$ groups. Preferred are $C_{1-6}$alkyl groups, especially methyl.

When $R^{11}$ and $R^{12}$ form the residue of an azacyclic ring system, the ring system suitably contains from 5 to 10 ring atoms, preferably 6, 7 or 8 ring atoms, more preferably 7 ring atoms.

When $R^{11}$ and $K^{12}$ together form the residue of an azabicyclic ring system, the azabicyclic ring system may be fused, spiro or bridged, preferably fused or bridged, more preferably bridged. The azabicyclic ring system may optionally be substituted by one or more $C_{1-4}$alkyl, such as methyl, groups. The alkyl substituents may be located on any available carbon atoms of the azabicyclic ring system. In particular, geminal disubstitution is provided for.

Preferably the azabicyclic ring system is unsubstituted.

Suitably the azabicyclic ring system contains from 7 to 10 ring atoms, preferably 7, 8 or 9 ring atoms.

Particularly preferred are compounds of formula (I) wherein $R^{11}$ and $R^{12}$ together form the residue of an azacyclic ring system substituted by one or more methyl groups, or $R^{11}$ and $R^{12}$ together form the residue of a bridged azabicyclic ring system, especially 3-azabicyclo[3.2.2]nonan-3-yl.

Particularly preferred are compounds of formula (I) wherein $R^3$ represents $C_{5-7}$cycloalkyl, especially cyclohexyl.

Preferably the salts of the compounds of formula (I) are pharmaceutically acceptable, but non-pharmaceutically acceptable salts may be used for the preparation of pharmaceutically acceptable salts. The pharmaceutically acceptable salts of the compounds of formula (I) include the conventional non-toxic salts or the quaternary ammonium salts of the compounds from formula (I) formed, e.g., from non-toxic inorganic or organic acids or bases. For example, such conventional non-toxic salts include those derived from inorganic acids such as hydrochloric, hydrobromic, sulphuric, sulphamic, phosphoric, nitric and the like; and the salts prepared from organic acids such as acetic, propionic, succinic, glycolic, steric, lactic, malic, tartaric, citric, ascorbic, palmoic, maleic, hydroxymaleic, phenylacetic, glutamic, benzoic, salicylic, sulphanilic, 2-acetoxy benzoic, fumaric, toluenesulphonic, methanesulphonic, ethane disulphonic, oxalic and isothionic.

The salts of the present invention can be synthesized from the compound of formula (I) which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The present invention also encompasses a pharmaceutical composition comprising a compound of formula (I), or a salt or prodrug thereof and a pharmaceutically acceptable carrier or diluent.

The compounds of formula (I) and their salts and prodrugs, may be administered to animals, preferably to mammals, and most especially to a human subject either alone or, preferably, in combination with pharmaceutically acceptable carriers or diluents, optionally with known adjuvants, such as alum, in a pharmaceutical compostion, according to standard pharmaceutical practice. The compounds can be administered orally, parenterally, including by intravenous, intramuscular, intraperitoneal or subcutaneous administration, or topically.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavouring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

For topical administration, a compound of formula (I) may be formulated as, for example, a suspension, lotion, cream or ointment.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) antagonise CCK and/or gastrin and are useful for the treatment and prevention of disorders including central nervous system disorders wherein CCK and/or gastrin may be involved. Examples of such disease states include gastrointestinal diseases, including gastrointestinal ulcers, such as peptic and duodenal ulcers, irritable bowel syndrome, gastroesophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved. Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate mediated, as well as anesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further by useful in the treatment of stress and its relationship with drug abuse.

The compounds of formula (I) may further be useful in the treatment of oncologic disorders wherein CCK may be involved. Examples of such oncologic disorders include small cell adenocarcinomas and primary tumours of the central nervous system glial and neuronal cells. Examples of such adenocarcinomas and tumours include, but are not limited to, tumours of the lower oesophagus, stomach, intestine, colon and lung, including small cell lung carcinoma.

The compounds of formula (I) may also be useful as neuroprotective agents, for example, in the treatment and/or prevention of neurodengenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of formula (I) may further be used to induce miosis for therapeutic purposes after certain types of examination and intraocular surgery. An example of intraocular surgery would include cateract surgery with implantation of an artificial lens. The CCK antagonist compounds of this invention can be used to prevent miosis occuring in association with iritis, ureitis and trauma.

The present invention therefore provides a compound of formula (I) or a salt or prodrug thereof for use in the preparation of a medicament.

The present invention also provides a compound of formula (I) for use in therapy.

In a further or alternative embodiment the present invention provides a method for the treatment or prevention of a physiological disorder involving CCK and/or gastrin which method comprises administration to a patient in need thereof of a CCK and/or gastrin antagonising amount of a compound of formula (I).

When a compound according to formula (I) is used as an antagonist of CCK or gastrin in a human subject, the daily dosage will normally be determined by the prescibing physician with the dosage generally varying according to the age, weight, and response of the individual patient, as well as the severity of the patient's symptoms. However, in most instances, an effective daily dosage wll be in the range from about 0.005mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, it may be necessary to use dosages outside these limits. For example, animal experiments have indicated that doses as low as 1 ng may be effective.

In effective treatment of panic syndrome, panic disorder, anxiety disorder and the like, preferably about 0.05 mg/kg to about 0.5 mg/kg of CCK antagonist may be administered orally (p.o.), administered in single or divided doses per day (b.i.d.). Other routes of administration are also suitable.

For directly inducing analgesia, anaesthesia or loss of pain sensation, the effective dosage preferably ranges from about 100 ng/kg to about 1 mg/kg by systemic administration. Oral administration is an alternative route, as well as others.

In the treatment or irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumour palliative for gastrointestinal neoplasma with gastrin receptors, as a modulator of central nervous activity, treatment of Zollinger-Ellison syndrome, or in the treatment of peptic ulcer disease, an effective dosage of preferably about 0.1 to about 10 mg/kg administered one-to-four times daily is indicated.

For use as neuroprotective agents the effective dosage preferably ranges from about 0.5 mg/kg to about 20 mg/kg.

Because these compounds antagonise the function of CCK in animals, they may also be used as feed additives to increase the food intake of animals in daily dosage of preferably about 0.05 mg/kg to about 50 mg/kg of body weight.

The compounds of formula (I) may be prepared from by reaction of intermediates of formula (II) with compounds of formula (III)

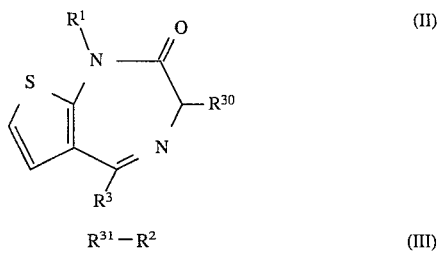

$R^{31} - R^2$  (III)

wherein $R^1$, $R^2$ and $R^3$ are as defined for formula (I) above, one of $R^{30}$ and $R^{31}$ represents $NH_2$ and the other of $R^{30}$ and $R^{31}$ represents —N=C=O.

The reaction is conveniently effected in a suitable organic solvent, such as an ether, for example, tetrahydrofuran.

Conveniently $R^{30}$ represents $NH_2$ and $R^{31}$ represents —N=C=O.

Intermediates of formula (II) wherein $R^{30}$ represents —N=C=O (hereinafter intermediates (IIB)) may be prepared from the corresponding compounds of formula (II) wherein $R^{30}$ is $NH_2$ (hereinafter intermediates (IIA)) by reaction with triphosgene in the presence of a base, such as a tertiary amine, for example, triethylamine. The reaction is conveniently effected in a suitable organic solvent, such as an ether, for example, tetrahydrofuran, suitably at low temperature, such as about 0° C. Intermediates of formula (III) wherein $R^{31}$ is —N=C=O (intermediates (IIIB)) may be prepared from the corresponding amines wherein $R^{31}$ is $NH_2$ (intermediates (IIIA)) analogously.

Intermediates of formula (IIA) may be prepared from compounds of formula (IV):

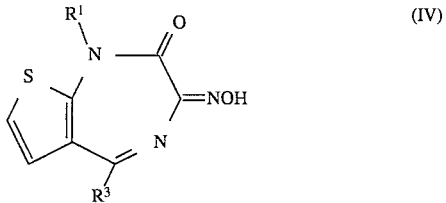

wherein $R^1$ and $R^3$ are as defined for formula (I) above, by reduction, for example, by catalytic hydrogenation or reduction using a suitable metal under acidic conditions.

Suitable hydrogenation catalysts include, for example, nobel metal catalysts, e.g. ruthenium, or rhodium which may be supported, for example, on carbon.

The reaction is preferably conducted in a suitable organic solvent, such as an alcohol, for example, methanol, at elevated temperature, e.g. about 60° C.

Suitable reduction methods using metals include, for example, the use of zinc and trifluoroacetic acid in a suitable solvent, such as acetic acid, preferably at elevated temperature, e.g. at about 40° C.

Intermediates of formula (IV) may be prepared from compounds of formula (V)

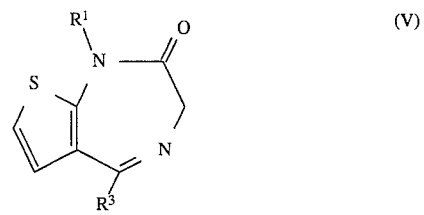

wherein $R^1$ and $R^3$ are as defined for formula (I), by reaction with isoamyl nitrite in the presence of a base.

Suitable bases of use in the reaction include alkali metal alkoxides, such as potassium t-butoxide.

Compounds of formula (V) wherein $R^3$ is $NR^{11}R^{12}$ may be prepared from compounds of formula (VI)

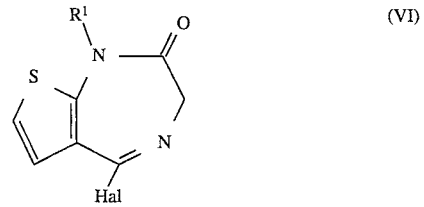

wherein $R^1$ is as defined for formula (I) and Hal represents halo, such as chloro, by reaction with an amine of formula $HNR^{11}R^{12}$.

Compounds of formula (V) wherein $R^3$ is cycloalkyl may be prepared from compounds of formula (VII)

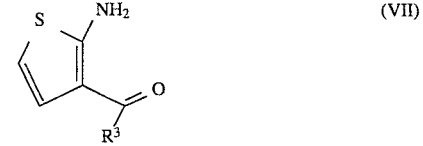

wherein $R^3$ is $C_{3-7}$cycloalkyl, by a reaction sequence comprising:

(i) reaction with a compound of formula Hal-COCH$_2$-Hal, wherein Hal represents halo, such as chloro or bromo, in the presence of a base, such as an organic base, for example pyridine. The reaction is conveniently effected in a suitable organic solvent, such as an ether, for example, diethyl ether.

(ii) Treatment with ammonia, conveniently in a suitable organic solvent, such as an alcohol, for example, methanol.

Compounds of formula (VII) may be prepared by reaction of intermediates of formula (VIII) with the compound of formula (IX)

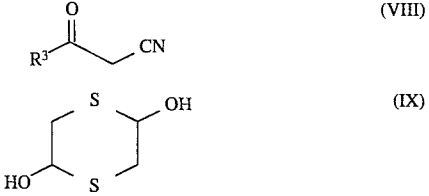

wherein $R^3$ is $C_{3-7}$cycloalkyl, in the presence of a base.

Suitable bases of use in the reaction include tertiary amines, for example, triethylamine.

The reaction is conveniently effected in a suitable organic solvent, such as an alcohol, for example, methanol.

Intermediates of formula (VIII) may be prepared from commercially availble compounds of formula $R^3CO_2R^{18}$ (wherein $R^3$ is $C_{3-7}$cycloalkyl and $R^{18}$ is alkyl) by treatment with butyl lithium and acetonitrile. The reaction is conveniently effected in a suitable organic solvent, such as an ether, for example, tetrahydrofuran, at low temperature, such as about −78° C.

The compound of formula (IX) is commerically available.

Intermediates of formulae (II), (IV) and (V) are novel compounds and form a further aspect of the present invention.

The present invention therefore provides intermediates of formula (A):

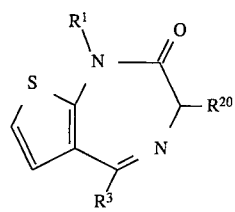

wherein $R^1$ and $R^3$ are as defined for formula (I) and $R^{20}$ represents H, NOH, —N=C=O or $NH_2$.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-L-tartaric acid and/or (+)-di-p-toluoyl-D-tartaric acid followed by fractional crystallization and regeneration of the free base. The novel compounds may also be resolved by formation of diastereomeric esters or amides, followed by chromatographic separation and removal of the chiral auxiliary. Alternatively, enantiomers of the novel compounds may be separated by HPLC using a chiral column.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following examples are provided to assist in a further understanding of the invention. Particular materials employed, species and conditions are intended to be further illustrative of the invention and not limitative of the scope thereof.

EXAMPLE 1

N-[3(R,S)-5-cyclohexyl-2,3-dihydro-1-methyl-2-oxo-1H-1,4-thienodiazepine-3-yl]-N'-(3-methylphenyl) urea a) 2-Amino-3-cyclohexanoyl-thiophene To a solution butyl lithium (160 ml of a 2.5 mol solution in hexane) in tetrahydrofuran (280 ml) at −780° C. was added acetonitrile (10.88 ml) over 15 mins. After stirring at −780° C. for 1 h, methyl cyclohexanecarboxylate (28.6 ml) was added dropwise over 15 mins. After 2h at −78° C., the reaction mixture was allowed to warm to room temperature and stirred for a further 1 h. Water (500 ml) was added to the mixture which was then washed with diethyl ether (2×500 ml). The aqueous solution was acidified to pill with concentrated hydrochloric acid and extracted with diethyl ether (2×500 ml). The combined organic layers were dried ($MgSO_4$), filtered and concentrated in vacuo to give an oil (28.2 g). This was dissolved in methanol (50 ml) with 2,5-dihydroxydithiane (14.22 g) and triethylamine (16 ml) was added dropwise. The reaction mixture was stirred overnight and the required product was collected by filtration (26.6 g): M.P. 148°–152° C., NMR δ ($CDCl_3$) 1.15–1.80 (10H, m), 2.79 (1H, m), 6.06 (1H, d, J=5.8 $H_z$), 6.71 (2H, br, s, $NH_2$), 6.90 (1H, d, J=5.8 $H_z$); MS (CI) m/e 210 $[MH]^+$.

b) 5-Cyclohexyl-2,3-dihydro-2-oxo-1,4-thienodiazenine

The product from step a) (26.6 g) was dissolved in diethyl ether (500 ml) with pyridine (10.17 ml) and bromoacetyl bromide (13.4 ml) was added dropwise at room temperature. When the addition was complete, the reaction mixture was stirred for 1 h at ambient temperature, then washed with water (2×200 ml), brine (1×200 ml), dried ($Na_2SO_4$), filtered and concentrated in vacuo. The residue was dissolved in methanol (600 ml) which had been presaturated with ammonia gas (200 ml) at −40° C. The solution was allowed to warm to room temperature and stirred for 14 h. The solvent was evaporated under vacuum and the residue was partitioned between dichloromethane (500 ml) and water (300 ml). The organic layer was washed with brine (1×200 ml), dried ($Na_2SO_4$), filtered and concentrated under vacuum. The residue was purified by chromatography on silica gel using hexane to 50% ethyl acetate in hexane as eluent to give the required product (4 g): MP 248° C. dec; NMR δ (DMSO) 1.16–1.71 (10H, m), 2.69 (1H, m), 3.99 (2H, s), 7.16 (2H, m), 11.07 (1H, br, s, NH); MS (CI) m/e 249 $[MH]^+$.

c) 5-Cyclohexyl-2,3-dihydro-1-methyl-2-oxo-1,4-thienodiazepine

The product from step b) (2.66 g) was dissolved in toluene (150 ml), heated to reflux and dimethyl formamide-dimethyl acetal (7.12 ml) was added dropwise. After heating under reflux for 1 h, the reaction mixture was allowed to cool and concentrated under vacuum. The residue was purified by silica gel chromatography (using 20% ethyl acetate in hexane to 50% ethyl acetate in hexane as eluent) to give the required product (2.8 g) NMR ($CDCl_3$) 1.16–1.81 (10H, m), 2.59 (1H, m), 3.43 (3H, s), 4.21 (2H, s), 7.00 (2H, s); MS (CI) m/e 263 $[MH]^+$.

d) 5-Cyclohexyl-1-methyl-3-hydroxyimino-2-oxo-1,4-thienodiazepine

The product from the previous reaction (3.33 g) was dissolved in toluene (100 ml), cooled to −20° C. and potassium tertiary butoxide (3.33 g) was added. After 20 minutes, isoamylnitrite (1.99 ml) was added and the reaction mixture was stirred at −20° C. in the dark for 18 h. 1 N Hydrochloric acid was added to quench the reaction and the mixture was partitioned between water (200 ml) and ethyl acetate (2×250 ml). The combined organic layers were dried ($MgSO_4$), filtered and concentrated under vacuum. The residue was purified by silica gel chromatography using 30–50% ethyl acetate in hexane as eluent to give the required product (1.1 g) NMR ($CDCl_3$) 1.89–1.96 (10H, m), 2.76 (1H, m), 3.53 (3H, s) 7.01 (2H, m), 7.96 (1H, br, s); MS (CI) m/e 292 $[MH]^+$.

e) N-[3(R,S)-5-Cyclohexyl-2,3-dihydro-1-methyl-2-oxo-1H-1,4-thienodiazepin-3-yl]-N'-(3-methylphenyl)urea The product from step d) (0.3 g) was dissolved in methanol (40 ml) and heated at 60° C. under 50 p.s.i. of hydrogen in the presence of 10% Rhodium on carbon catalyst (0.3 g) for 6h. The reaction mixture was filtered and concentrated under vacuum. The residue was dissolved in tetrahydrofuran (30 ml) and meta tolylisocyanate (0.133 ml) was added. The reaction mixture was stirred at room temperature for 14h then concentrated under vacuum. The residue was purified using 20–30% ethyl acetate in hexane as eluent to give a product which was recrystallised using diethyl ether/petrol 60–80 to give the title compound (41 mg): MP 190° C. (sub); NMR (DMSO) 1.02–1.99 (10H, m), 2.23 (3H, s), 2.74 (1H, m), 3.40 (3H, s) 5.11 (1H, d, J=8.4 Hz), 6.73 (1H, d, J=8.4 Hz), 7.08–7.46 (6H, m), 8.86 (1H, s); MS (CI) m/e 411 [MH]$^+$; Found C, 64.44; H, 6.51; N, 13.66. $C_{22}H_{26}N_4O_2S$ requires C, 64.36; H, 6.38; N, 13.65%.

EXAMPLE 2A

Tablets containing 1–25 mg of compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 2B

Tablets containing 26–100 mg of compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 3

Parenteral injection

| Compound of formula (I) | Amount mg 1 to 100 |
| --- | --- |
| Citric Acid Monohydrate | 0.75 |
| Sodium Phosphate | 4.5 |
| Sodium Chloride | 9 |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 4

Topical formulation

| Compound of formula (I) | Amount mg 1–10 |
| --- | --- |
| Emulsifying Wax | 30 |
| Liquid paraffin | 20 |
| White Soft Paraffin | to 100 |

The white soft paraffin is heated until molten. The liquid paraffin and emulsifying wax are incorporated and stirred until dissolved. The compound of formula (I) is added and stirring continued until dispersed. The mixture is then cooled until solid.

BIOLOGICAL ACTIVITY

The CCK-A and CCK-B antagonising activity of the compounds described herein was evaluated using the assays described in published European patent application no. 0514133. The method essentially involves determining the concentration of the test compound required to displace 50% of the specific $^{125}$I-CCK from rat pancreas (CCK-A) or guinea pig brain (CCK-B). The data in Table 1 were obtained for the compound of Example 1.

TABLE I

CCK RECEPTOR BINDING RESULTS
$IC_{50}$ (nM)

| Compound of Ex # | $^{125}$I-CCK Pancreas | $^{125}$I-CCK Brain |
| --- | --- | --- |
| 1 | 6.7 | 46 |

We claim:

1. A compound of Formula (I) or a pharmaceutically acceptable salt thereof:

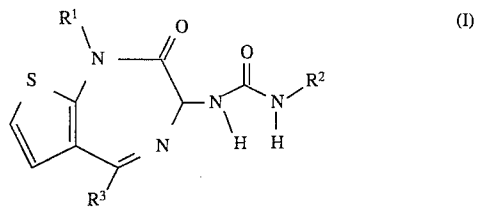

wherein:

$R^1$ represents H, $C_{1-6}$alkyl optionally substituted by one or more halo, $C_{3-7}$cycloalkyl, cyclopropylmethyl, $CH_2CO_2R^5$ (where $R^5$ is $C_{1-4}$alkyl) or $CH_2CONR^6R^7$ (where $R^6$ and $R^7$ each independently represents H or $C_{1-4}$alkyl, or $R^6$ and $R^7$ together form a chain $(CH_2)_p$ where p is 4 or 5);

$R^2$ represents a phenyl group optionally substituted by one or more substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, $(CH_2)_q$-imidazolyl, $(CH_2)_q$triazolyl (where q is 0, 1, 2 or 3), 5-hydroxy-4-pyrone, $NR^6R^7$, $NR^9COR^5$, $NR^9COR^{9'}R^5$ (where $R^9$ and $R^{9'}$ are each independently H or $C_{1-4}$alkyl), $CONR^6R^7$ (where $R^6$ and $R^7$ are as previously defined), $SO(C_{1-6}$alkyl), $SO_2(C_{1-6}$alkyl), trifluoromethyl, $CONHSO_2R^8$, $SO_2NHCOR^8$ (where $R^8$ is $C_{1-6}$alkyl, optionally substituted aryl being phenyl optionally substituted by a substitutent selected from the group consisting of: $C_{1-4}$alkyl, $C_{1-4}$alkoxy, halo and trifluoromethyl; 2,2-difluorocyclopropane or trifluoromethyl), $SO_2NHR^{10}$ (where $R^{10}$ is a nitrogen containing heterocycle selected from the group consisting of: thiazole, thiadiazole, and pyrazino), $B(OH)_2$, $(CH_2)_qCO_2H$, where q is as previously defined; or $R^2$ represents a group

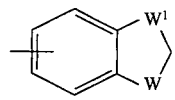

where W represents $CH_2$ or $NR^9$, where $R^9$ is as previously defined and $W^1$ represents $CH_2$, or W and $W^1$ each represent O; and $R^3$ represents $C_{3-7}$cycloalkyl optionally substituted by one or more $C_{1-4}$alkyl groups, or $R^3$ is $NR^{11}R^{12}$, where $R^{11}$ and $R^{12}$ each independently represent H; $C_{1-12}$alkyl optionally substituted by $NR^9R^{9'}$ (where $R^9$ and $R^{9'}$ are as previously defined) or an azacyclic selected from morpholinyl and piperidinyl or azabicyclic group selected from 3-aza-bicyclo[3.2.2]nonan-3-yl; $C_{4-9}$cycloalkyl optionally substituted by one or more $C_{1-4}$alkyl groups; $C_{4-9}$cycloalkyl$C_{1-4}$alkyl optionally substituted in the cycloalkyl ring by one or more $C_{1-4}$alkyl groups; optionally substituted aryl which is selected from the group consisting of: phenyl, thienyl, furyl, pyrrolyl and pyridyl, which can be substituted with a group selected from the group consisting of: $C_{1-4}$alkyl, $C_{1-4}$alkoxyl, halo and trifluoromethyl; optionally substituted aryl$C_{1-6}$alkyl wherein optionally substituted aryl is defined immediately prior; or azacyclic or azabicyclic groups as defined above; or $R^{11}$ and $R^{12}$ together form the residue of an optionally substituted azacyclic or azabicyclic ring system selected from 3-azabicyclo[3.2.2]nonan-3-yl.

2. A compound as claimed in claim 1 wherein $R^1$ represents $C_{1-6}$alkyl, $C_{3-7}$cycloalkyl, cyclopropylmethyl, $CH_2CO_2R^5$ or $CH_2CONR^6R^7$; $R^2$ represents a phenyl group optionally substituted by one or more substituents selected from $C_{1-6}$alkyl, halo, hydroxy, $C_{1-4}$alkoxy, $(CH_2)_q$-tetrazolyl optionally substituted in the tetrazole ring by $C_{1-4}$alkyl, $(CH2)_q$imidazolyl, $(CH_2)_q$triazolyl (where q is 0, 1, 2 or 3), 5-hydroxy-4-pyrone, $NR^6R^7$, $NR^9COR^5$, $NR^9COR9'R^5$ (where $R^9$ and $R^{9'}$ are each independently H or $C_{1-4}$alkyl) $CONR^6R^7$ (where $R^6$ and $R^7$ are as previously defined), $SO(C_{1-6}$alkyl), $SO_2(C_{1-6}$alkyl), trifluoromethyl, $CONHSO_2R^8$, $SO_2NHCOR^8$ (where $R^8$ is $C_{1-6}$alkyl, optionally substituted aryl as defined above in claim 1, 2,2-difluorocyclopropane or trifluoromethyl), $SO_2NHR^{10}$ (where $R^{10}$ is a nitrogen containing heterocycle as defined above in claim 1), $B(OH)_2$, $(CH_2)_rCO_2H$, where r is 0, 1 or 2; or $R^2$ represents a group

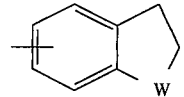

where W represents $CH_2$ or $NR^9$; and $R^3$ represents $C_{3-7}$cycloalkyl or $NR^{11}R^{12}$, where $R^{11}$ and $R^{12}$ each independently represent H, $C_{1-12}$alkyl, $C_{4-9}$cycloalkyl, optionally substituted aryl as defined above in claim 1, optionally substituted aryl$C_{1-6}$alkyl as defined above in claim 1 or azacyclic or azabicyclic groups as defined above in claim 1, or $R^{11}$ and $R^{12}$ together form the residue of an azacyclic or a bridged azabicyclic ring system as defined above in claim 1; or pharmaceutically acceptable salts thereof.

3. A compound as claimed in claim 1 wherein $R^1$ is $C_{1-6}$alkyl.

4. A compound as claimed in claim 1 wherein $R^1$ is $C_{1-6}$alkyl substituted by one or more halo.

5. A compound as claimed in claim 1 wherein $R^2$ represents 5-indanyl or phenyl substituted by methyl.

6. A compound as claimed in claim 1 wherein $R^3$ represents $NR^{11}R^{12}$ and $R^{11}$ and $R^{12}$ together form the residue of an azacyclic ring system as defined above in claim 1 substituted by one or more methyl groups, or $R^{11}$ and $R^{12}$ together form the residue of a bridged azabicyclic ring system as defined above in claim 1.

7. A compound as claimed in claim 1 wherein $R^3$ represents $C_{5-7}$cycloalkyl.

8. A compound as claimed in claim 1 selected from N-[3(R,S)-5-cyclohexyl-2,3-dihydro-1-methyl-2-oxo-1H-1,4-thienodiazepine-3yl-]-N'-(3-methylphenyl)urea; or pharmaceutically acceptable salts thereof.

9. A pharmaceutical composition comprising a compound as claimed in claim 1 in association with a pharmaceutically acceptable carrier.

\* \* \* \* \*